US012744116B2

(12) United States Patent
Teixeira et al.

(10) Patent No.: US 12,744,116 B2
(45) Date of Patent: Sep. 22, 2026

(54) WHOLE-BODY ANATOMICAL DIGITAL TWIN FROM PARTIAL MEDICAL IMAGES

(71) Applicant: Siemens Medical Solution USA, Inc., Malvern, PA (US)

(72) Inventors: Brian Teixeira, Lawrence Township, NJ (US); Shikha Chaganti, Princeton, NJ (US); Daphne Yu, Yardley, PA (US); Ankur Kapoor, Plainsboro, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 660 days.

(21) Appl. No.: 18/184,889

(22) Filed: Mar. 16, 2023

(65) Prior Publication Data

US 2024/0312603 A1 Sep. 19, 2024

(51) Int. Cl.
*G16H 30/40* (2018.01)
*G06T 7/00* (2017.01)

(52) U.S. Cl.
CPC ........... *G16H 30/40* (2018.01); *G06T 7/0012* (2013.01); *G06T 2207/20081* (2013.01)

(58) Field of Classification Search
None
See application file for complete search history.

(56) References Cited

U.S. PATENT DOCUMENTS

| | | | |
|---|---|---|---|
| 11,478,212 B2 | 10/2022 | Singh et al. | |
| 2017/0091939 A1* | 3/2017 | Kluckner | G06T 19/00 |
| 2018/0228460 A1* | 8/2018 | Singh | G01R 33/5608 |
| 2021/0358595 A1* | 11/2021 | Tamersoy | G06T 17/00 |
| 2023/0267671 A1* | 8/2023 | Kim | G06T 7/70<br>345/473 |
| 2024/0013415 A1* | 1/2024 | Tam | G06V 40/10 |
| 2026/0076745 A1* | 3/2026 | Decrouez | A61B 34/10 |

OTHER PUBLICATIONS

Keller, Marilyn, et al. “OSSO: Obtaining skeletal shape from outside.” Proceedings of the IEEE/CVF conference on computer vision and pattern recognition. 2022. (Year: 2022).*

Hauri, Pascal, et al. “Development of whole-body representation and dose calculation in a commercial treatment planning system.” Zeitschrift für medizinische Physik 32.2 (2022): 159-172. (Year: 2022).*

Pommert, Andreas, et al. “Creating a high-resolution spatial/symbolic model of the inner organs based on the Visible Human.” Medical Image Analysis 5.3 (2001): 221-228. (Year: 2001).*

Raju, Ashwin, et al. “Deep implicit statistical shape models for 3d medical image delineation.” proceedings of the AAAI conference on artificial intelligence. vol. 36. No. 2. 2022. (Year: 2022).*

(Continued)

*Primary Examiner* — Samah A Beg

(57) ABSTRACT

For generating and/or machine training to generate a whole-body representation of a patient, one or more partial-body scans or images of the patient are extrapolated to the whole-body representation of both interior and exterior anatomy. One or more machine-learned models (e.g., per-organ-group implicit generative shape models) fill the whole-body representation based on the partial information from imaging.

16 Claims, 4 Drawing Sheets

(56) References Cited

OTHER PUBLICATIONS

Siemens Healthineers USA, “AI-Rad Companion” retrieved Mar. 7, 2023: a href=“https://www.siemens-healthineers.com/en-us/digital-health-solutions/digital-solutions-overview/clinical-decision-support/ai-rad-companion” target=“_blank” https://www.siemens-healthineers.com/en-us/digital-health-solutions/digital-solutions-overview/clinical-decision-support/ai-rad-companion/a pp. 1-8.

* cited by examiner

WHOLE-BODY ANATOMICAL DIGITAL TWIN FROM PARTIAL MEDICAL IMAGES

BACKGROUND

The present embodiments relate to generating a whole-body digital twin. A whole-body model may be a highly valuable tool in medical education by simulating physical training environments in virtual spaces such as virtual reality, augmented reality, mixed reality, or metaverse. Medical education applications include surgical training with simulated real patient data and development of other hand skills such as physical examinations and nursing training. With reliability of the model, such a technology may also facilitate remote doctor's office visits and even remote surgery with the use of real-time imaging to simulate the patient in a virtual space.

Various approaches have been used to create a whole-body model. For example, the skin of a patient is pictured. The picture is used to extrapolate interior organs. As another example, a full-body scan of one modality may be used to extrapolate a full-body representation in a different modality (e.g., magnetic resonance to computed tomography). As yet another example, weight, height, gender, and/or other patient characteristics are used to personalize a generic or statistical whole-body model. These approaches may result in a poor or inaccurate representation, not include details, and/or require information not available.

SUMMARY

Systems, methods, and computer readable media with stored instructions are provided for generating and/or machine training to generate a whole-body representation of a patient. One or more partial-body scans or images of the patient are extrapolated to the whole-body representation of both interior and exterior anatomy. One or more machine-learned models are used to fill the whole-body representation based on the partial information from imaging.

In a first aspect, a method is provided for generating a whole-body representation of a patient. At least one medical image representing only part of a patient is acquired. A representation of a whole body of the patient is generated from the at least one medial image representing only part of the patient. The representation of the whole body represents interior and exterior anatomy of the patient and is generated, at least in part, by a machine-learned model.

In one implementation, just the at least one medical image representing only part of the patient is acquired. The representation of the whole body is generated from just the at least one medical image.

In another implementation, a part of the representation of the whole body of the patient is not represented in any information used to generate the representation of the whole body. The at least one medical image does not represent the part of the representation of the whole body.

According to one implementation, the at least one medical image represents one or more first organs, a part of one or more second organs, and skin of the patient. The at least one medical image does not represent one or more third organs. The representation is generated as including the skin, the first organs, the second organs, and the third organs.

In yet another implementation, anatomy of the part of the patient represented in the at least one medical image is segmented. The segmented anatomy is input to the machine-learned model, which outputs part of the representation of the whole body not represented in the input. For example, the anatomy is segmented as a first organ, part of a second organ, and skin. The machine-learned model outputs the entire second organ in response to input of the first organ, part of the second organ, and the skin.

As another implementation, the machine-learned model is a per-organ group implicit generative shape model. In one implementation, the machine-learned model is an autodecoder.

In an implementation, the representation is generated with optimization of a latent vector by sampling in three-dimensional space in a trained manifold.

According to an implementation, the representation is generated by estimating shapes of surrounding organs to first shapes represented in the at least one medical image. The estimating occurs recursively using the machine-learned model for a first organ group and a second machine-learned model for another organ group. The shapes of the surrounding organs and the first shapes are included in the representation of the whole body of the patient. In one example, the machine-learned model and the second machine-learned model are in a hierarchy of models for the whole body.

As another implementation, a shape of a same organ is generated multiple times as part of a recursive operation. A representation for the same organ is formed from the shapes of the multiple times based on recursion depth of the recursive operation.

In one implementation, signed distance functions are generated for the interior anatomy by the machine-learned model.

In another implementation, the machine-learned model outputs the representation of the whole body as a single output.

In yet another implementation, skin is reconstructed as the exterior anatomy of the whole body. The skin is used to enforce consistency for generating of the interior anatomy not represented in the at least one medical image.

In a second aspect, a method is provided for machine training generation of a whole-body avatar from partial medical imaging. Different organ groups for different partial medical imaging regions are assigned to per-organ group implicit generative shape models. For each of the per-organ group implicit generative shape models, points are sampled in three-dimensional space and signed distance functions of the points to surfaces of a three-dimensional model of the organ group are estimated. The surfaces are for the organ group. While sampling, a latent vector representing the three-dimensional model in a trained manifold is optimized. The per-organ group implicit generative shape models as trained by the optimizing are stored.

According to one implementation, for each of the per-organ group implicit generative shape models, multiple of the signed distance functions are estimated, one of the signed distance functions for an organ not or only partially represented in the partial medical imaging region. The per-organ group implicit generative shape models together form the whole-body avatar.

As another implementation, the optimizing includes assigning a random vector in the trained manifold.

As an implementation, for each of the per-organ group implicit generative shape models, multiple the signed distance functions are estimated for multiple organs and a skin surface.

In a third aspect, a medical imaging system is provided. A medical imager is configured to scan only part of a patient. An image processor is configured to form a whole-body avatar from the scan of only part of the patient. The whole-body avatar is formed by a first machine-learned implicit generative shape model optimization of a latent vector to segmentations from the scan.

In one implementation, the whole-body avatar is formed by multiple machine-learned implicit generative shape models including the first machine-learned implicit generative shape model. Different ones of the multiple machine-learned implicit generative shape models form different organs of the whole-body avatar in a hierarchy of related organs.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

A whole-body anatomical digital twin is generated from partial-body medical images. The digital twin is generated from partial-body medical images with per-group of organs implicit generative models forming a hierarchy for the whole-body model. A whole-body avatar depicts both the internal and external anatomy from partial medical imaging. An anatomically correct digital twin of a patient is generated using partial scans only. Any kind of 3D acquisition, such as computed tomography (CT), magnetic resonance (MR), or positron emission tomography (PET), representing just a region of the patient may be used to generate the whole-body digital twin. The digital twin has a high degree of fidelity to external appearance as well as internal organs based on medical imaging.

The generated whole-body model may be helpful for surgery training, intervention planning, and/or medical education by simulating physical environments in virtual spaces, such as virtual reality, augmented reality, mixed reality, or metaverse. Medical education applications include surgical training with simulated real patient data and development of other hand skills, such as physical examinations and nursing training. With reliability of the personalized whole-body model, such a technology could also facilitate remote doctor's office visits and remote surgery with the use of real-time imaging to simulate the patient in a virtual space. The whole-body model may be used in a patient facing healthcare application, such as creating a digital twin of the individual, which digital twin mirrors the real-life patient both externally and internally, based on available medical imaging. Other health and wellness, virtual physician consultation, and/or patient education may benefit from having this digital twin.

Figure 1:
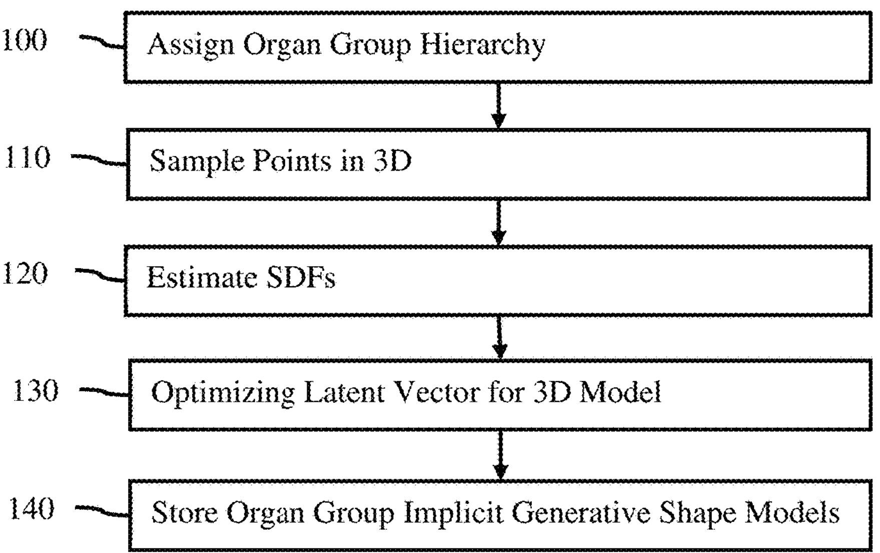
FIG. 1 is a flow chart diagram of one implementation of a method for machine training for generation of a whole-body avatar from partial medical imaging.

FIG. 1 is a flow chart diagram of one embodiment of a method for machine training generation of a whole-body avatar from partial medical imaging. A hierarchical approach relating different organs with each other generates a whole-body avatar depicting external body shape as well as internal anatomy from partial-body images. An implicit generative shape model is machine trained for each of different organ groups corresponding to organ groupings in different or typical partial-body medical scans.

Medical image is used for an output image in display format or data representing the patient to be processed into the display format. For example, a medical image may be scan data representing different locations in and/or on the patient formatted or distributed in the scan format rather than the display format. This medical image may be at any of various parts of the processing or imaging pipeline, such as prior to or after filtering, scan conversion, three-dimensional rendering, and/or detection.

The method of FIG. 1 is performed by an image processor, computer, server, or another processor or processors. A medical scanner may acquire the partial-body medical image and/or perform segmentation. The image processor may acquire the medical image from memory or a database and/or perform segmentation. The image processor stores the trained machine-learned model in a memory.

Additional, different, or fewer acts may be provided. For example, act 100 is not performed where one three-dimensional or patient model is used instead of the hierarchy of models. As another example, acts for scanning patients and/or collecting data for machine training may be provided.

The acts are performed in the order shown (top to bottom or numerical) or another order. For example, acts 110, 120, and/or 130 are performed interleaved with or simultaneously with each other as the machine learning. As another example, acts 110, 120, and/or 130 are performed together or in an opposite order.

For machine training, many samples of training data are acquired or accessed. The training data includes partial scans or organ segmentations from the partial scans and ground truth organ distributions for the whole body or grouped organs of the whole body. The ground truth and/or partial scans may be by groups, such as abdomen, chest, head, legs, and arms. The ground truth may be relative segmentations of organs and/or other anatomy by region or group so that the collection represents the whole body or may be for the whole body as a single three-dimensional model. The examples below will use organs as the anatomy.

Segmentation provides the surface of the organ or other anatomy. Alternatively, the segmentation indicates voxels or locations for that organ or anatomy, such as each having a volume. The segmentation is in three dimensions either as a boundary or surface or as a volume.

In act 100, an organ group hierarchy is assigned. A user or programmer inputs to the image processor the hierarchy. Alternatively, the image processor groups based on partial scans available in the training data.

The grouping may be organs of the whole body in one group. To reduce the processing and size of the resulting implicit generate shape model, multiple groupings of different organs are used in the hierarchy. The hierarchy is a spatial or grouping relationship of sub-sets of organs together. For example, one grouping is of organs of the abdomen. Another grouping is organs of the chest. Other groups may be the head, arms, and legs. Any number and/or types of organs may be represented, such as larger organs. The bones and/or muscles may or may not be included. The skin may be included as an organ. Different parts of the skin may be included in different groupings.

In one implementation, the different organ groups are assigned based on or for different partial medical imaging regions. For example, an abdomen scan may represent the kidney, liver, and part of the lungs. These three organs are grouped since they are represented in that type of partial scan. A chest scan may include the lungs and heart. These two organs are grouped since they are represented in that type of partial scan. An organ may be in different groupings.

Within a grouping, a hierarchy may be provided. For example, partial scans that typically include full organs result in the full organ as primary and any partial organs as linked secondary. Any hierarchy between groups and/or within groups may be used.

The different organ groups are assigned to different per-organ group implicit generative shape models. Different such models may be used within a given group, such as using pair-wise models. A separate three-dimensional model is learned or machine trained for each pair or group of organs. Models are provided as a collection that together then represents the whole body, such as interior organs and the exterior anatomy (e.g., skin and/or landmarks). The per-organ group implicit generative shape models together form the whole-body avatar. Based on how organs are distributed in partial medical images based on scan protocols, a hierarchy of organs is defined to link the organs pairwise or groupwise based on how often they appear (fully or partially) in the same scan. Pairwise will be used in examples below (i.e., an implicit generative shape model trained for every unique pair of organs. Other equal (three or four organs) or unequal groups (e.g., paired organs and triplet organs in different groups) for each model may be used.

Using a large (hundreds or thousands) collection of partial 3D scans and extracted organ segmentations, a per-organ-pair implicit generative shape model is trained. The same scans may be used for other pairs of organs and corresponding shape models. Different partial scans may be used for other pairs and corresponding shape models.

The skin is or is not included in any given grouping. In one implementation, the skin or part of the skin is treated as one of the organs. In another implementation, the skin is included as a reference without being one of the organs in the pair. In this approach, a triplet of two organs together with the external skin surface are used for the per-organ-pair implicit generative shape model. This approach could be extended to a larger number of neighboring organs with the skin.

The partial medical images (medical images of only a part of the patient less than the whole body) may be used as inputs to the model for machine learning. In one implementation, the organs represented in the partial medical images are segmented. The segmentation is used as the input to the model for machine learning. Any segmentation may be used, such as random walker, filtering and thresholding, pattern matching, fitting, or a machine-learned segmentation. Different segmentation may be used for different organs, such as applying organ specific segmentation. Segmentation masks are used for training.

Partial medical images often depict whole organs as well as partial organs. For example, abdominal scans might fully depict liver and kidneys but only partially cover lungs. As a result, the segmentation provides both full organ segmentation (e.g., liver and kidney segmentation masks) as well as partial organ segmentation (e.g., segmentation mask for the part of the lungs in the medical image).

Figure 2:
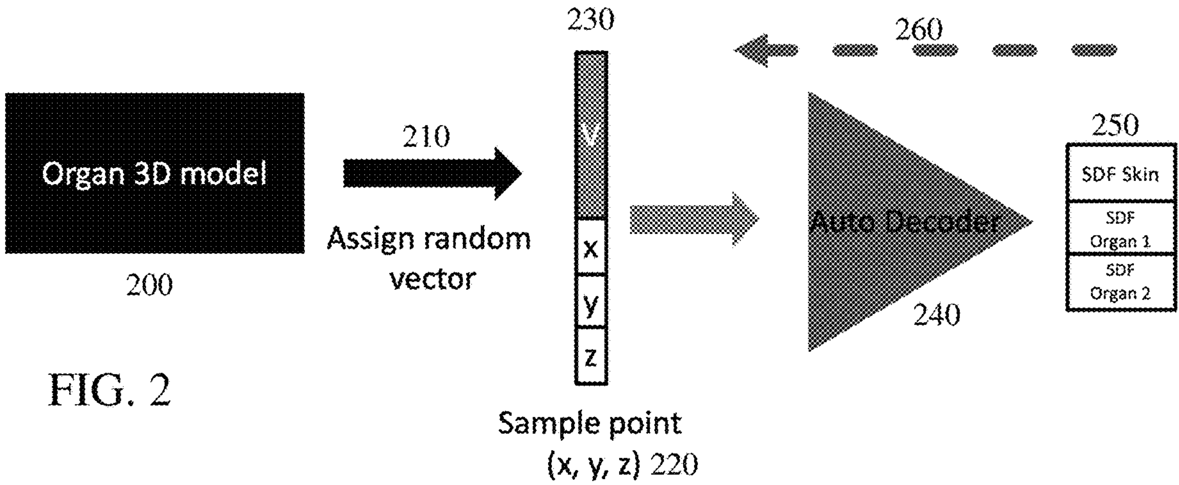
FIG. 2 illustrates an example implementation of machine training of an organ-group implicit generative shape model.

Acts 110, 120, 130, and 140 are performed for each of the per-organ group (e.g., each of the per-organ-pair group) implicit generative shape models. Acts 110, 120, and 130 provide or are the machine learning. FIG. 2 shows an example training of the implicit generative shape model. An organ three-dimensional model 200 represents the possible organs and skin for the model. A manifold is learned so that a vector 230 for that manifold space may be selected. The vector 230 is a latent representation of an instance of the organs in the space of all possible organ arrangements for that group. An initial selection 210 may be random. Alternatively, the initial selection is based on other information such as skin location.

In act 110, the image processor samples points (x, y, z) in three-dimensional space. A uniform, random, or other sampling pattern may be used. The sampling may be guided based on known organ shapes and/or locations, such as for the organs with a full segmentation. In FIG. 2, the sampling is represented by the x, y, z included with the selected vector 230. A sequence of different locations is used in the sampling.

In act 120, the image processor estimates signed distance functions (SDFs) for each sampling location. The SDFs are signed distances from the points to the surfaces of the organs in the three-dimensional model. The surfaces being estimated are the ones in the three-dimensional model (i.e., the organs of the group for that implicit generative shape model). For each of the per-organ group implicit generative shape models, multiple of the signed distance functions are estimated for each sample location. In the example of FIG. 2, an autodecoder 240 receives the vector 230 and the sample location (x, y, z) as input to output three SDFs 250, one for skin, one for one organ (e.g., liver) and one for another organ (e.g., lungs or kidney). The SDFs 250 are for full organs. One or more of the SDFs 250 may be for an organ not or only partially represented in the partial medical image or imaging region. For example, one SDF 250 is for the entire lung surface despite only part of the lungs being in the medical image. As another example, one SDF 250 is for the heart, which is not represented at all in the partial medical image. Where the skin surface is included in the implicit generative shape model, the SDF 250 for the part of the skin near or within the partial scan region or for the entire patient is estimated. The per-organ-pair implicit generative shape model is trained by sampling points in 3D space and estimating the SDFs of a given point to the organ and/or skin surfaces of the 3D model 200. Since each model is trained on two organs as well as the skin surface in one implementation, the model outputs not one but three SDF values.

The machine training trains the autodecoder 240, which is formed from layers of a neural network that receives the latent space of the vector 230 and a position in space to output the SDF of the organ at the position. A convolutional neural network, fully connected neural network, Densenet, or other autodecoder architecture may be used. The machine training learns the values of learnable parameters of the autodecoder 240.

By sampling a region, the full volume may be reconstructed from the output SDFs. Referring to FIG. 2, differences from ground truth SDFs for a given sampling point given a particular one of the training samples (segmentations) are used to provide errors 260 for optimizing the autodecoder 240 across the set of training data. The training teaches the autodecoder 240 to correlate between the skin and the organs using the SDFs.

In act 130 of FIG. 1, the image processor also learns implicitly. The latent vector representation of the three-dimensional model 200 is optimized for a trained manifold. The manifold for the latent representation is learned. While optimizing the latent vector 230 representing the 3D model in the trained manifold (manifold being learned), the sampling and errors 260 are used to identify and/or create vectors in the latent space for each of the training samples. For each sample, different vectors 230 are searched to locate the optimum vector 230 for that sample. The initial one may be randomly selected or selected based on another criterion.

At training time, there is a joint optimization of the learned space (represented by the training of autodecoder 240) as well as the latent vectors 230 for each of the training samples. At inference time, the learned space in the form of the autodecoder 240 is fixed, and only the latent vector 230 is optimized.

Once the manifold space and autodecoder 240 are learned, the resulting machine-learned model (e.g., the per-organ-pair implicit generative shape model) is stored in act 140. For the whole-body representation, the collection of machine-learned models is stored. Each machine learned model is trained to generate a shape of partially or unseen organ or organs given a seen and/or partially seen segmentation. These machine-learned models may be used to provide the shapes, including size and location, of organs relative to each other in the hierarchy for each group, leading to a collection for the whole-body.

Figure 3:
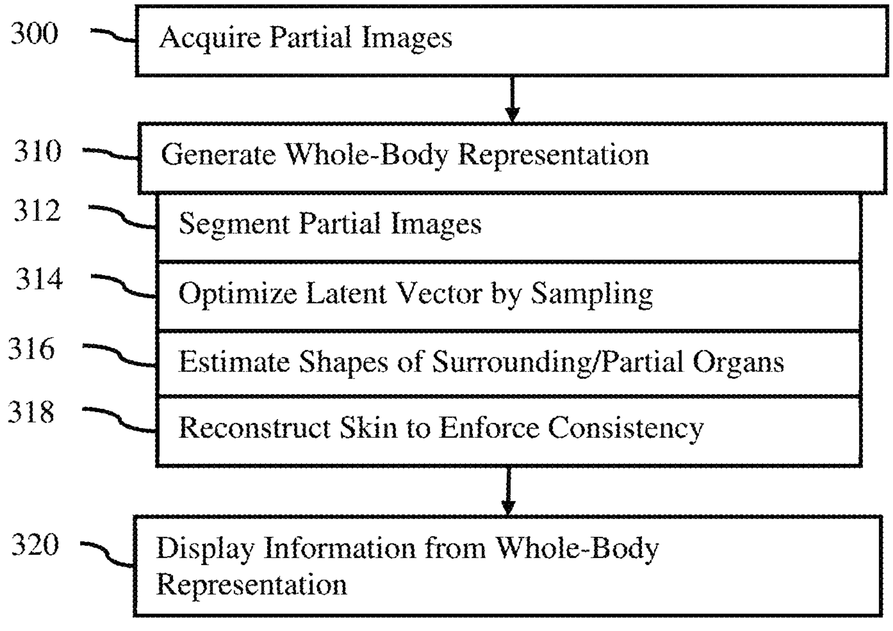
FIG. 3 is a flow chart diagram of one implementation of a method for generating a whole-body representation of a patient.

FIG. 3 shows one implementation of a flow chart of a method for generating a whole-body representation of a patient. The implicit generative shape model or models as trained are applied to infer organ shapes for the whole body of the patient.

A medical imager or scanner performs act 300. Alternatively, an image processor acquires the partial images by transfer over a network and/or access to a memory or database. The image processor performs acts 310-318. A display device, under the control of the image processor or another processor, performs act 320. Other devices may perform any of the acts.

Additional, different, or fewer acts may be provided. For example, act 318 is not provided. The acts are performed in the order shown (top to bottom or numerical), but other orders may be used. For example, acts 312, 314, and 316 are interleaved in any order and/or performed simultaneously.

In act 300, a medical scanner or image processor acquires at least one medical image representing only part of a patient. The medical image or images are acquired by scanning a patient or loading from memory.

The medical image or images represent only part of the patient. Where multiple images are acquired, the images represent a same or different region or part of the patient. For example, two different medical images representing an abdomen region are acquired. As another example, one image representing a chest and another representing the abdomen are acquired. The medical images are partial, such as representing all or most of one or more organs (e.g., kidney and liver) and/or part of one or more organs (e.g., part of lungs). The partial medical images do not represent all of one or more organs and/or do not represent any of one or more organs. For example, an abdomen scan may not represent part of the lungs and any of the heart.

The partial medical images fail to represent the entirety of the patient. One or more organs are only partially or not at all represented in all of the partial medical images. Alternatively, a collection of different medical images represent together at least part of all of the organs of interest for the whole-body model.

One, more, or all the partial medical images represent part of the skin. For example, an abdomen scan represents skin of the abdomen but not elsewhere. As another example, a chest scan represents skin of the chest. Skin of all or parts of the arms and/or legs may be represented in the chest or lower abdomen medical image. In an alternative, a camera captures the skin of the patient, such as for a front surface from head to toe. This capture may occur during a scan for a partial medical image so that the skin as captured corresponds to or is locatable relative to the organs in the partial medical image.

In act 310, the image processor generates a representation of a whole body of the patient from the medial image or images representing only part or parts of the patient. Available scans for the patient rather than a whole-body scan are used to estimate the shape of surrounding organs. The shape, size, and/or position of organs fully represented in any partial medical images are used. The shape, size, and/or position of organs only partly represented and/or not represented at all in the medical images are inferred using the machine-trained models (e.g., per-organ-groupwise implicit generative shape models). Alternatively, the shape, size, and/or position of organs fully represented in one or more partial medical images are, at least in part, also inferred using the machine-trained models.

The whole body is represented. The whole-body representation may be a collection of internal organs with shape, size, and position of the organs provided. Additionally, the whole-body representation may include both interior and exterior anatomy, such as organs of interest for interior anatomy and skin or skin landmarks are the exterior anatomy. The whole-body representation may not include information of no interest, such as some organs, some exterior landmarks, and/or some skin regions. The whole body may be represented with some parts represented with less resolution or more abstractly than others.

The whole-body representation is generated from just partial medical images. At least one part of the whole-body representation is inferred by the machine-learned model. At least one part of the whole-body representation (e.g., an organ or part of an organ) is represented in any information used to generate the representation of the whole body. The partial medical image or images do not represent at least part of the representation of the whole body. The whole-body representation is generated as including organs fully represented, organs partially represented, and/or organs not represented at all in the partial medical images. The whole-body representation may include the skin or exterior landmarks. Part of the skin or skin landmarks may be represented or not represented in the partial medical images.

A machine-learned model or models generate the whole-body representation. The machine-learned model or models are per-organ group implicit generative shape models. Each includes an autodecoder. Other decoders may be used. A neural network, support vector machine, decision trees, Bayesian network, or other machine-learned model may be used.

For the per-organ group models, the models were trained to output organ position, size, and/or shape for one or more organs given inputs. The inputs may be images or segmentations from the images that represent all, part, or none of one or more organs. The outputs are organs only partially or not at all represented in the input. Organs represented in the input may be output. In one embodiment, the output is a signed distance function. Iterative sampling with the trained model is used to determine the organ segmentations as an output.

Figure 4:
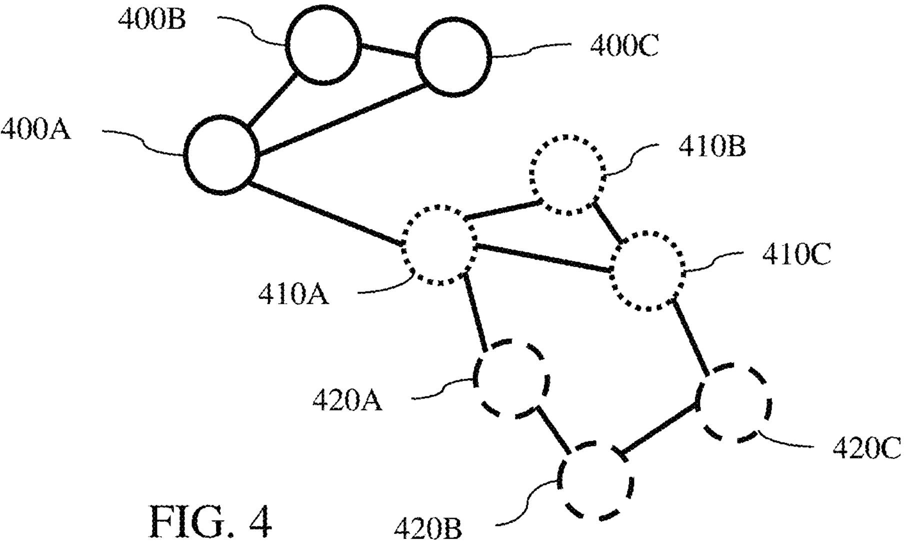
FIG. 4 illustrates example recursive assembly of a whole-body model from partial imaging.

The per-organ grouping provides for different machine-learned models for different organ groups. FIG. 4 shows an example. A partial lower abdomen medical image provides full segmentations for the intestines 420B and stomach 420C but only partial segmentation for the liver 420A. A partial chest medical image provides full segmentations for the heart 400B and lungs 400C but only partial for the liver 400A. The kidneys 410B and spleen 410C are not at all represented in either partial image. Part of the liver 410A is not represented in either partial image.

Each line in FIG. 4 indicates a per-organ pairwise implicit generative shape model. Each groupwise model provides shapes for groups of organs. Each pairwise model provides shapes for two organs. For example, one pairwise model is provided for each link or line of FIG. 4. The machine-learned models may also receive as input and/or provide output for the skin.

Acts 312-318 of FIG. 3 represent an implementation using implicit generative shape models. The operation of one model linking two organs and part of the skin is used as an example herein. Other models are used for other organs. Models for larger groups of organs may be used. Models without skin information may be used. Where both organs are represented in a partial medical image, the corresponding machine-learned model may not be used at all. Alternatively, the model is still used to identify a vector in latent space that may be used for initializing other models and/or to provide refinements to segmentation.

In act 312, the image processor segments any anatomy (e.g., organs) represented in the medical images acquired in act 310. Any segmentation may be used, such as applying machine-learned segmentation.

Any anatomy of interest fully or partially represented in a given medical image is segmented. For example, anatomy for two organs (e.g., heart and lungs) and anatomy for part of an organ (e.g., liver) are segmented. The skin represented in the image may or may not be segmented.

In acts 314 and 316, the image processor inputs the segmented anatomy to the machine-learned model. The model then outputs an estimation of shape, position, and/or size of one or more other organs. For implicit generation, the input of the segmentation is used to match with the vector in the learned manifold in latent space, and the output by the model is of SDFs used with sampling to form the representation of anatomy to be assembled as part of the whole-body representation. The segmentation is input but not used directly as an input to the autodecoder 240. The segmentation is used as a ground truth for the optimization of the latent vector 230. The autodecoder 240 outputs the SDF for part of the organ for which the the ground truth is known from the segmentation. The prediction of the SDF or organ formed from SDFs and an SDF from the ground truth or the ground truth are used to compute the loss between both and backpropagate to the latent vector 230. This process is repeated for all points in the segmentation. Using the machine-learned model and sampling, the entirety of an organ only partially represented or not represented at all in the medical image or segmentations is output. The machine-learned model and sampling may output information used for the input anatomy, other anatomy, and skin.

In act 314, the image processor optimizes the latent vector by sampling at different locations. The sampling is in three-dimensional space using any pattern. The output SDFs for the machine-learned model are used to optimize the fit of the known segmentations for that machine-learned model to the vector in latent space. The sampling in space optimizes the latent vector in the trained manifold. The vector corresponding to the organ arrangement for the patient represented by the input segmentations is identified by the optimization.

In act 316, the image processor estimates shapes, size, and/or location of organs or other anatomy. Shapes of surrounding organs relative to shapes represented in the medical image are estimated. The estimation occurs recursively using the machine-learned model for an organ group. The estimation for the same and/or different organs or other anatomy uses other machine-learned models for others organ groups. These estimated shapes, position, and/or location of the surrounding organs for the different models are included in the representation of the whole body of the patient.

As represented in FIG. 4, the links represent a hierarchy of model for the whole body. Optimization and estimation are recursively applied using the different models to build up the whole body. Newly generated organs may be used to generate yet further organs. For example, the model for 400A-410A estimates the shape of the liver 410A from the segmentation of the partial liver 400A and/or from the heart 400B. This liver 410A is used to estimate the shapes of the kidneys 410B. These shapes of the kidneys 410B is used to estimate the shape of the spleen 410C. This hierarchy of anatomy is used to generate the shape, position, and/or size of interior organs for the whole body. The skin or exterior anatomy may be likewise estimated using the hierarchy for different parts of the skin.

As an alternative or generic illustration, each node of the graph of FIG. 4 is an organ. The edges connecting two nodes represent organs connected in the hierarchy, and thus represented in pair in a generative model. Here, a first partial scan depicts the three organs 400A-C, and a second partial scan represents three organs 420A-C. Other organs 410A-C are estimated using models connecting them to organs visible with partial scans (400A-410A model, 420A-410A model, 420C-410C model, 410A-410B model, 410A-410C model, and 410C-410B model).

By following the heirarchy, the shape, position, and/or size of a given organ may be generated multiple times. One or more may be wholly or at least in part based on segmentation of that organ as represented in a medical image. Others or all may be estimated using models. The recursive operation may form represenations (e.g., segmentations) for an organ multiple times. Since organs may be paired multiple times (for example, liver could be connected to lungs as well as kidneys), different models could output different SDFs for a given 3D point and a given organ.

In one approach, the different representations of the same organ are combined, such as averaged. In another approach, one of the representations is selected. As one implementation, the image processor forms a representation for the organ from the shapes of the multiple times based on recursion depth of the recursive operation. The initial depth is the segmentation from an image. If such segmentation exists, that segmentation is selected. If such segmentation does not exist, the representation estimated using the fewest number of links in the hierarchy is selected. In a similar approach, the actual SDF to use is defined using a voting algorithm, such as random sample consensus (RANSAC), weighted with the uncertainty of the prediction. The uncertainty is derived as or by the recursion depth. The uncertainty is based on the number of models used to get to the representation or estimation of SDF.

The skin or parts of the skin represented in the medical image or images may be used in the estimation of act 316. This forms the SDF for parts of the skin to be used in the whole body and/or assists in accurate estimation for interior organs.

In act 318, the skin is used to enforce consistency. A camera, such as a depth camera, captures a two- or three-dimensional representation of the skin of the patient, at least from one camera view. The skin is reconstructed in three dimensions as the exterior anatomy for the whole-body representation. The reconstructed skin is used as input to the models with any skin segmented in the medical images to enforce consistency in the estimation across models (through the hierarchy). The consistency is enforced with the reconstructed skin for generating the interior anatomy not represented entirely or at all in the medical images.

The estimated organs or other anatomy from the hierarchy are collected or assembled together. The result is the whole-body representation. By recursively progressing through the models, the whole-body avatar is created. The whole body includes organs or other anatomy of interest and may include the skin or exterior landmarks of interest. All the body from head to toe is represented using the per-organ-group implicit generative shape models.

In an alternative implementation, the image processor uses a machine-learned model that was trained to output all the components of the whole-body representation. One machine-learned model outputs the entire whole-body representation rather than using a hierarchy of models. The whole body is provided as a single output based on optimization and estimation using the input of the segmentations. Instead of using a hierarchical model, a model representing all organs is used.

In act 320, the image processor generates an output image. The output image is loaded into a display plane of a display screen and output for diagnosis, prognosis, training, simulation, virtual reality, or other purpose.

The output image shows information from the whole-body representation. A cross-section, three-dimensional rendering, or other imaging (e.g., multi-planar reconstruction) of the whole-body representation is output. The user may interact with the output, such as shifting perspective or cross-section. The image is altered to show this interaction.

The output image represents the whole body of the patient rather than a generic whole body. Other generic or patient-fit information may be included, such as fitting biomechanical models for different organs to the estimated organs of the whole-body representation.

A whole-body model may be used in medical education by simulating physical training environments in virtual spaces such as virtual reality, augmented reality, mixed reality, or metaverse. Medical education applications include surgical training with simulated real patient data and development of other hand skills such as physical examinations and nursing training. Remote doctor's office visits and even remote surgery with the use of real-time imaging may use the whole-body model to simulate the patient in a virtual space.

Figure 5:
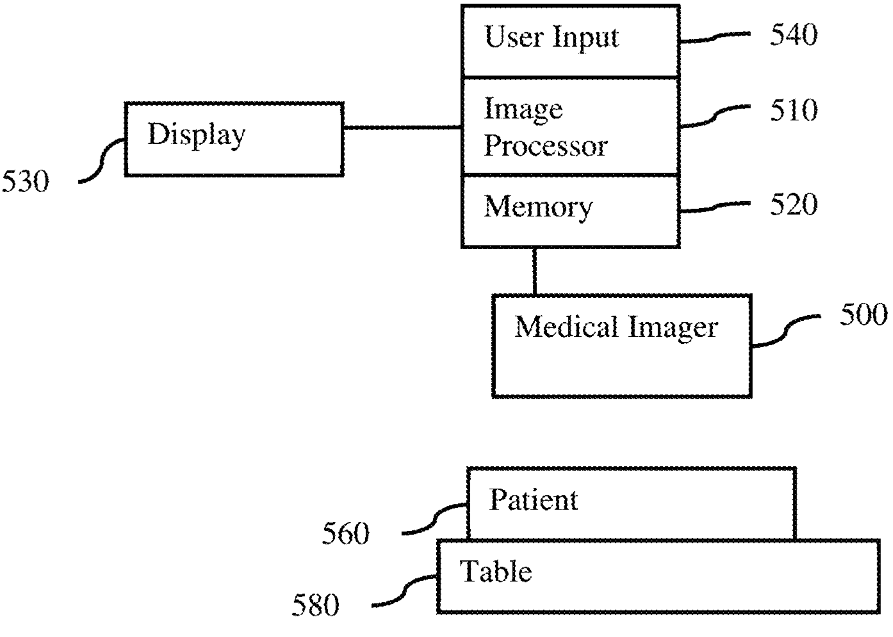
FIG. 5 is a block diagram of one embodiment of a medical imaging system for generating a whole-body avatar from partial imaging.

FIG. 5 shows one embodiment of a medical imaging system for generating a digital twin of a patient. The medical imaging system includes the display 530, user input 540, memory 520, and image processor 510. The display 530, image processor 510, and memory 520 may be part of the medical imager 500, a computer, server, workstation, or another system for image processing medical images from a scan of a patient. A workstation or computer without the medical imager 500 may be used as the medical imaging system.

Additional, different, or fewer components may be provided. For example, a computer network is included for remote capture of partial scan data or images. As another example, one or more machine-learned segmentors or classifiers are applied to segment organs in medical images.

The medical imager 500 is an x-ray, computed tomography, magnetic resonance, ultrasound, positron emission tomography, single photon emission computed tomography, or another type of medical imager. The medical imager 500 operates pursuant to one or more settings to position and operate a detector relative to the patient. The settings control the location or region of the patient being scanned and the scan sequence. The medical imager is configured by the settings to scan only part of a patient. For example, a scan is directed to an organ, organ group, or region (e.g., chest, abdomen, lower abdomen, head, or pelvic). This scan results in scan data that represents only part of the patient, such as representing 25%, 50%, 75% or fewer of entire organs of the patient or organs of interest in a whole-body model.

The patient 560 on the table 580 is imaged by the medical imager 500 using the settings. The medical imager 500 generates partial medical image or images of the patient. More than one organ, organ group, or region may be scanned. For one organ, organ group, or region, one or more images are acquired. As a collection, the partial scans do not represent the whole body of the patient. At least one organ of interest in the whole-body model is only partly represented or not represented at all. The collection may only represent 25%, 50%, 75% or fewer of the entire organs of the patient or organs of interest in a whole-body model.

The user input 540 is configured, through a user interface operated by the image processor 510 or another processor, to receive and process user input. For example, indication of the type of partial scan and/or selection of the patient and corresponding available medical images are input. The user input 540 is a device, such as keyboard, button, slider, dial, trackball, mouse, or another device).

The image processor 510 is a control processor, general processor, digital signal processor, three-dimensional data processor, graphics processing unit, application specific integrated circuit, field programmable gate array, artificial intelligence processor, digital circuit, analog circuit, combinations thereof, or another now known or later developed device for image processing. The image processor 510 is a single device, a plurality of devices, or a network. For more than one device, parallel or sequential division of processing may be used. Different devices making up the image processor 510 may perform different functions, such as segmenting organs or landmarks in partial images by one device and generating a whole-body avatar from the segmentations by another device. In one implementation, the image processor 510 is a control processor or other processor of a medical imager 500. The image processor 510 operates pursuant to and is configured by stored instructions, hardware, and/or firmware to perform various acts described herein.

In one implementation, the image processor 510 is configured to form a whole-body avatar from the scan of only part of the patient. The whole-body avatar is formed by a machine-learned implicit generative shape model optimization of a latent vector to segmentations from the scan. The whole-body avatar is formed by a single shape model. Alternatively, the whole-body avatar is formed from multiple machine-learned implicit generative shape models. Different ones of the multiple machine-learned implicit generative shape models form different organs or groups of organs of the whole-body avatar in a hierarchy of related organs.

Figure 6:
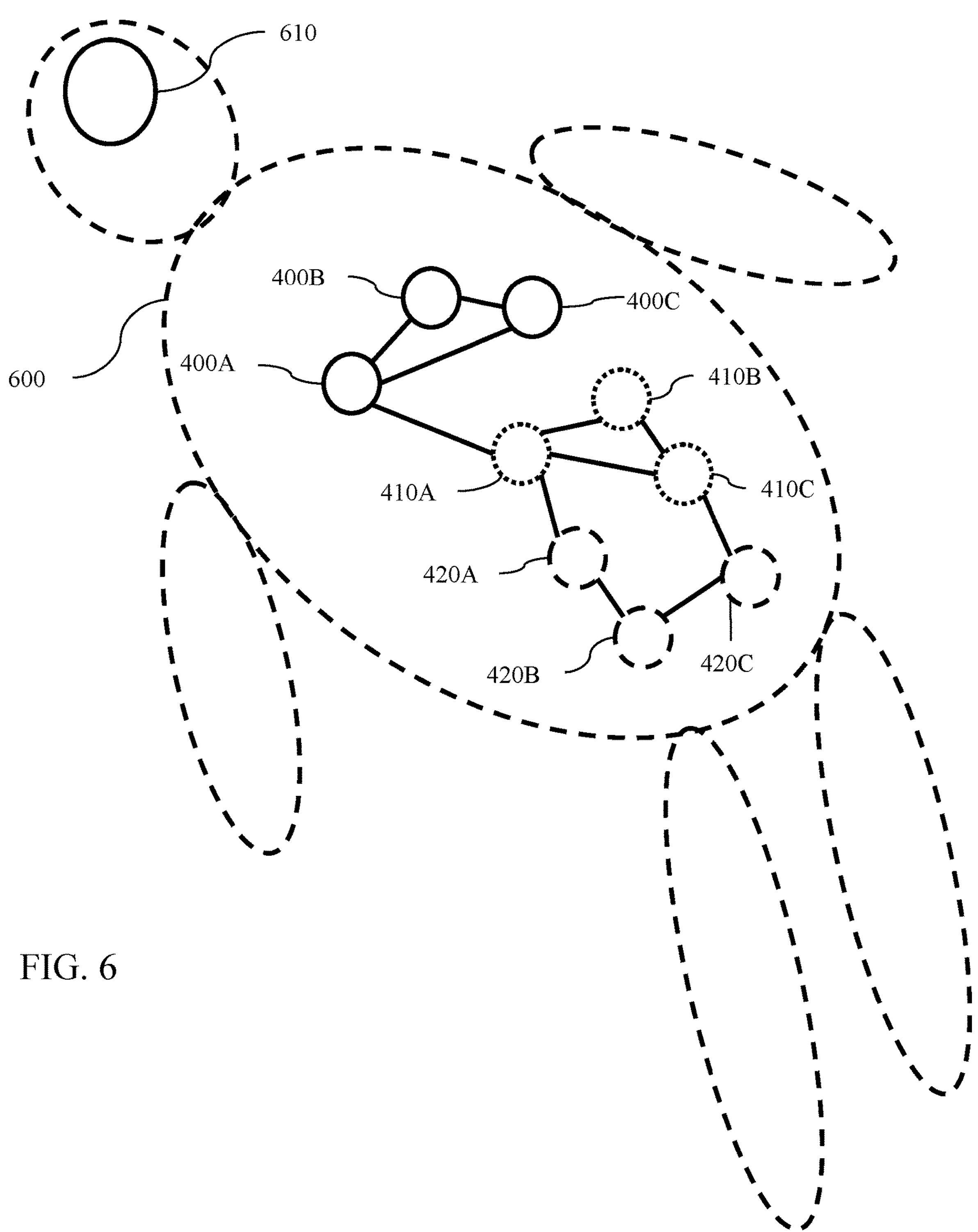
FIG. 6 illustrates an example whole-body avatar.

FIG. 6 shows an example whole-body avatar 600 shown in cross-section. The avatar 600 may be two or three dimensional. The avatar 600 includes the organs 400-420 as represented in FIG. 4 plus an additional organ 610. The skin is represented as a dashed line. Bones, muscle, or other soft tissue may be represented. The whole body of the patient is represented. This whole body is more than the organs represented in the partial image. The whole body may include the entire skin, including feet and hands. The whole body includes organs of interest. Fewer than all organs existing in a person may form the whole-body representation. For example, the organs discussed for FIG. 4 are used as the internal organs without the organ 610. Alternatively, all the organs of the body are included.

The image processor 510 is configured to generate an output. Information is extracted from the whole-body avatar 600 to form an image. For example, the whole-body avatar 600 is represented in a surgical training simulation. As another example, the whole-body avatar 600 is used for virtual, augmented, mixed, or other reality imaging. The whole-body avatar 600 or part thereof may be displayed as a two or three-dimensional representation.

The display 530 is a CRT, LCD, projector, plasma, printer, tablet, smart phone, or another now known or later developed display device for displaying whole-body avatar 600 or information extracted from the whole-body avatar 600.

The instructions for implementing the methods, processes, and/or techniques discussed herein are provided on non-transitory computer-readable storage media or memories, such as a cache, buffer, RAM, removable media, hard drive or other computer readable storage media (e.g., the memory 520). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for generating a whole-body representation of a patient, the method comprising:

acquiring at least one medical image representing only part of a patient, the at least one medical image representing one or more first organs, a part of one or more second organs, and skin of the patient, the at least one medical image not representing one or more third organs; and generating a representation of a whole body of the patient from the at least one medial image representing only part of the patient, the representation of the whole body representing interior and exterior anatomy of the patient, the representation generated, at least in part, by a machine-learned model, wherein generating the representation of the whole body comprises generating the representation as including the skin, the first organs, the second organs, and the third organs.

2. The method of claim 1 wherein acquiring comprises acquiring just the at least one medical image representing only part of the patient and wherein generating comprises generating from just the at least one medical image.

3. The method of claim 1 wherein generating comprises generating where a part of the representation of the whole body of the patient is not represented in any information used to generate the representation of the whole body, the at least one medical image not representing the part of the representation of the whole body.

4. The method of claim 1 wherein generating comprises generating with the machine-learned model comprising a per-organ group implicit generative shape model.

5. The method of claim 1 wherein generating comprises generating with the machine-learned model comprising an autodecoder.

6. The method of claim 1 wherein generating comprises optimizing a latent vector by sampling in three-dimensional space in a trained manifold.

7. The method of claim 1 wherein generating comprises generating a shape of a same organ of the second organs multiple times as part of recursive operation and forming a representation for the same organ from the shapes of the multiple times based on recursion depth of the recursive operation.

8. The method of claim 1 wherein generating comprises generating signed distance functions for the interior anatomy by the machine-learned model.

9. The method of claim 1 wherein generating comprises generating by the machine-learned model outputting the representation of the whole body as a single output.

10. The method of claim 1 wherein generating comprises reconstructing the skin as the exterior anatomy of the whole body and enforcing consistency with the skin for generating of the interior anatomy not represented in the at least one medical image.

11. A method for generating a whole-body representation of a patient, the method comprising:

acquiring at least one medical image representing only part of a patient; and generating a representation of a whole body of the patient from the at least one medical image representing only part of the patient, the representation of the whole body representing interior and exterior anatomy of the patient, the representation generated, at least in part, by a machine-learned model, wherein generating comprises segmenting anatomy of the part of the patient represented in the at least one medical image, the segmented anatomy used in optimization with the machine-learned model, the machine-learned model outputting information used to form part of the representation of the whole body not represented in the input.

12. The method of claim 11 wherein segmenting comprises segmenting the anatomy as a first organ, part of a second organ, and skin, and wherein the machine-learned model outputs the information for the entire second organ in response to input of the first organ, part of the second organ, and the skin.

13. A method for generating a whole-body representation of a patient, the method comprising:

acquiring at least one medical image representing only part of a patient; and generating a representation of a whole body of the patient from the at least one medical image representing only part of the patient, the representation of the whole body representing interior and exterior anatomy of the patient, the representation generated, at least in part, by a machine-learned model, wherein generating comprises estimating shapes of surrounding organs to first shapes represented in the at least one medical image, the estimating occurring recursively using the machine-learned model for a first organ group and a second machine-learned model for another organ group, the shapes of the surrounding organs and the first shapes included in the representation of the whole body of the patient.

14. The method of claim 13 wherein the machine-learned model and the second machine-learned model are in a hierarchy of models for the whole body.

15. A medical imaging system comprising:

a medical imager configured to scan only part of a patient;

an image processor configured to form a whole-body avatar from the scan of only part of the patient, the whole-body avatar formed by a first machine-learned implicit generative shape model optimization of a latent vector to segmentations from the scan.

16. The medical imaging system of claim 15 wherein the whole-body avatar is formed by multiple machine-learned implicit generative shape models including the first machine-learned implicit generative shape model, different ones of the multiple machine-learned implicit generative shape models forming different organs of the whole-body avatar in a hierarchy of related organs.

* * * * *